United States Patent [19]

Zinnes et al.

[11] 4,188,482
[45] Feb. 12, 1980

[54] THIAZINO INDOLE COMPOUNDS

[75] Inventors: Harold Zinnes, Rockaway; Martin L. Schwartz, Parsippany, both of N.J.

[73] Assignee: Warner-Lambert Company, Morris Plains, N.J.

[21] Appl. No.: 902,584

[22] Filed: May 4, 1978

[51] Int. Cl.$^2$ .................. A61K 31/54; C07D 513/04
[52] U.S. Cl. .................. 544/32; 260/326.12 R; 424/246
[58] Field of Search .................. 260/326.5 B; 544/56, 544/32

[56] References Cited

U.S. PATENT DOCUMENTS

| | | | |
|---|---|---|---|
| 3,904,617 | 9/1975 | Pelz | 260/243 R |
| 3,912,729 | 10/1975 | Demerson | 260/243 R |
| 4,056,537 | 11/1977 | Demerson | 260/326.5 B |
| 4,066,763 | 1/1978 | Demerson | 424/246 |

Primary Examiner—Alton D. Rollins
Assistant Examiner—Lisa Jones
Attorney, Agent, or Firm—David B. Ehrlinger; Stephen Raines

[57] ABSTRACT

3,4-Dihydro-10-[2-(dialkylamino)ethyl]-1-phenyl-1H-thiazino[4,3-a]indol-4-ol compounds having in free base form the formula

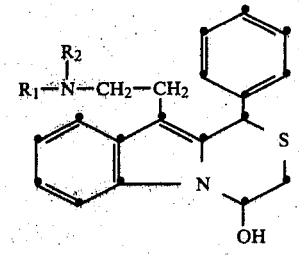

I where $R_1$ and $R_2$ are lower alkyl groups. The compounds of this invention exhibit anti-allergy properties and are indicated in the management of allergy.

8 Claims, No Drawings

THIAZINO INDOLE COMPOUNDS

SUMMARY AND DETAILED DESCRIPTION

The present invention relates to 3,4-dihydro-10-[2-(dialkylamino)ethyl]-1-phenyl-1H-thiazino[4,3-a]-indol-4-ol compounds having in free base form the formula

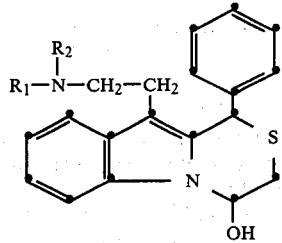

I where $R_1$ and $R_2$ are lower alkyl groups, that is, straight or branched chain alkyl groups of 1 to 6 carbon atoms such as methyl, ethyl, propyl, isopropyl, n-butyl, n-amyl, n-hexyl, and 2,3-dimethylbutyl.

The above compounds are characterized by antiallergy properties in mammals. Thus, in a routine test conducted according to procedures described in I. Mota, Life Sciences, 7,465 (1963) and Z. Ovary, O. Bier, Proc. Soc. Exptl. Biol. Med., 81,584 (1952), the compound of formula I where $R_1$ and $R_2$ are methyl groups prevents allergic and asthmatic reactions in rats at a dosage level of about 25 mg./kg. intraperitoneally. These compounds are, therefore, indicated in the management of bronchial asthma, hay fever and other similar allergic conditions.

The compounds of the present invention can be administered orally and by such compositions as tablets, pills, dispersible powders and the like. The active ingredient is mixed with at least one inert pharmaceutical diluent such as lactose and suitable granules, using agents such as water or alcohol, and the resulting granules compressed into tablets utilizing standard tableting procedures.

Liquid pharmaceutically administrable compositions are prepared by dissolving or suspending the active ingredient in a pharmaceutically acceptable carrier such as water or syrup. In addition, the compounds of this invention can be administered by inhalation therapy in which the compound is formulated by standard aerosol technique.

To treat allergic manifestations the compounds of this invention are typically administered in dosages varying between 10–25 mg. per kg. of body weight 2 to 3 times daily. The precise dosage regimen can be varied depending on the mode of administration and the condition being treated, using procedures which are conventional in the healing arts.

According to the process of this invention, a quaternary salt of formula

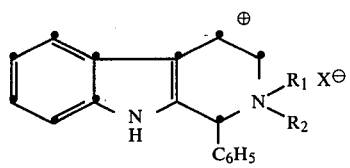

II where $R_1$ and $R_2$ have the above-specified significance and $X^-$ is a halide, sulfate or sulfonate anion, is reacted at ambient temperature with diethylmercaptoacetal in the presence of a base such as sodium hydride in a solvent consisting of a mixture of tetrahydrofuran (THF) with one or more non-hydroxylic polar solvents such as hexamethylphosphorous triamide (HMPA), dimethylformamide (DMF), and dimethylsulfoxide (DMSO). The resulting intermediate acetal of formula

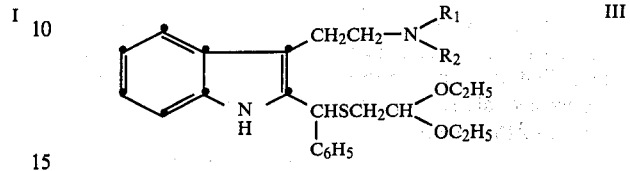

III where $R_1$ and $R_2$ have the same significance, is treated with dilute aqueous hydrochloric acid to cause hydrolysis of the acetal function, and the resulting aldehyde of formula

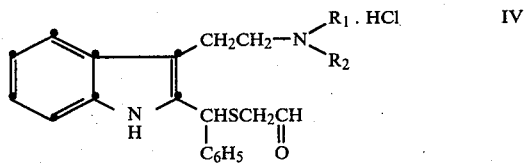

IV where $R_1$ and $R_2$ have the same significance, is treated with alkali to produce the desired final product.

The starting materials are commercially available except those having formula II which are prepared as described by Hoshino et al., Ann. 516, 76 (1935), and Julian et al., J.A.C.S. 57, 539 (1935), which description is incorporated herewith by reference.

The compounds of the invention form salts with pharmaceutically acceptable acids and these salts are included within the scope of the invention. These salts include, for example, salts formed with acids such as hydrochloric, sulfuric, nitric and acetic acid and the like.

The invention is illustrated by the following examples.

EXAMPLE 1

To a slurry of sodium hydride (1.85 g., 0.044 M, 57% mineral oil dispersion), in tetrahydrofuran (100 ml.), at 25° C., was slowly added a solution of diethylmercapto acetal (6.6 g., 0.044 M) in tetrahydrofuran (100 ml.). Solid 3,4-dihydro-2,2-dimethyl-1-phenyl-1H,9H-pyrido-[3,4-b]indolium iodide (16.16 g., 0.04 M) and hexamethylphosphorous triamide (50 ml.) were added after the hydrogen evolution ceased, and the reaction mixture was stirred at 25° C., for 2 hours the reaction mixture was poured into water (1000 ml.) and extracted with ether (700 ml.). The organic layer was washed successively with two portions of water and with saturated sodium chloride solution, dried over sodium sulfate, and evaporated to give the acetal intermediate 15.2 g. (89%).

To a solution of the acetal (12 g., 0.0281 M) in 1,4-dioxane (140 ml.) was added 4 N aqueous hydrochloric acid solution (140 ml.) and the cloudy mixture was stirred at 25° C. for 0.5 hours. The reaction mixture was poured into 1 N sodium hydroxide solution (500 ml.), containing ice (100 g.), to give the desired product, 3,4-dihydro-10-[2-(dimethylamino)ethyl]-1-phenyl-1H- thiazino[4,3-a]indol-4-ol; m.p. 143°–146° C. after recrystallization from acetonitrile.

The corresponding hydrochloride salt is obtained by dissolving the free base in ether, treating the solution with dry hydrogen chloride until precipitation of the product is complete, and isolating the product. The hydrobromide and sulfate are obtained by treating the free base in ether solution with dry hydrogen bromide or with sulfuric acid.

Following the procedure of Example 1 but replacing the 2,2-dialkyl quaternary salt starting material with an equivalent amount of a different 2,2-dialkyl substituted quaternary salt starting material provides other compounds of the invention as follows:

|     | Starting Material | Product |
| --- | --- | --- |
| (a) | 3,4-Dihydro-2,2-diethyl-1-phenyl-1H,9H-pyrido-[3,4-b]indolium iodide | 3,4-Dihydro-10-[2-(diethylamino)ethyl]-1-phenyl-1H-thiazino[4,3-a]indol-4-ol |
| (b) | 3,4-Dihydro-2,2-di-(n-propyl)-1-phenyl-1H,9H-pyrido[3,4-b]indolium iodide | 3,4-Dihydro-10-[2-[di-(n-propyl)amino]ethyl}-1-phenyl-1H-thiazino-[4,3-a]indol-4-ol |
| (c) | 3,4-Dihydro-2,2-diisopropyl-1-phenyl-1H,9H-pyrido-[3,4-b]indolium iodide | 3,4-Dihydro-10-[2-(diisopropylamino)ethyl]-1-phenyl-1H-thiazino[4,3-a]indol-4-ol |
| (d) | 3,4-Dihydro-2,2-dibutyl-1-phenyl-1H,9H-pyrido-[3,4-b]indolium iodide | 3,4-Dihydro-10-[2-(dibutylamino)ethyl]-1-phenyl-1H-thiazino[4,3-a]indol-4-ol |
| (e) | 3,4-Dihydro-2,2-diamyl-1-phenyl-1H,9H-pyrido-[3,4-b]indolium iodide | 3,4-Dihydro-10-[2-(diamylamino)ethyl]-1-phenyl-1H-thiazino[4,3-a]indol-4-ol |
| (f) | 3,4-Dihydro-2,2-dihexyl-1-phenyl-1H,9H-pyrido-[3,4-b]indolium iodide | 3,4-Dihydro-10-[2-(dihexylamino)ethyl]-1-phenyl-1H-thiazino[4,3-a]indol-4-ol |
| (g) | 3,4-Dihydro-2,2-di-(2,3-dimethylbutyl)-1-phenyl-1H,9H-pyrido[3,4-b]indolium iodide | 3,4-Dihydro-10-{2-[di-(2,3-dimethylbutyl)amino]ethyl}-1-phenyl-1H-thiazino-[4,3-a]indol-4-ol |

We claim:
1. A compound of the formula

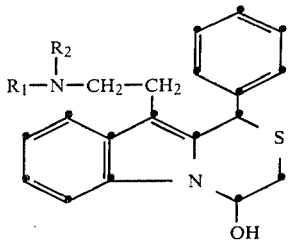

where $R_1$ and $R_2$ are alkyl groups having 1 to 6 carbon atoms and the corresponding pharmaceutically acceptable acid addition salts.

2. A compound according to claim 1 which is 3,4-dihydro-10-[2-(dimethylamino)ethyl]-1-phenyl-1H-thiazino[4,3-a]indol-4-ol.

3. A compound according to claim 1 which is 3,4-dihydro-10-[2-(diethylamino)ethyl]-1-phenyl-1H-thiazino[4,3-a]indol-4-ol.

4. A compound according to claim 1 which is 3,4-dihydro-10-{2-[di-(n-propyl)amino]ethyl}-1-phenyl-1H-thiazino[4,3-a]indol-4-ol.

5. A compound according to claim 1 which is 3,4-dihydro-10-[2-(dibutylamino)ethyl]-1-phenyl-1H-thiazino-[4,3-a]indol-4-ol.

6. A compound according to claim 1 which is 3,4-dihydro-10-[2-(diamylamino)ethyl]-1-phenyl-1H-thiazino-[4,3-a]indol-4-ol.

7. A compound according to claim 1 which is 3,4-dihydro-10-[2-(dihexylamino)ethyl]-1-phenyl-1H-thiazino-[4,3-a]indol-4-ol.

8. A compound according to claim 1 which is 3,4-dihydro-10-{2-[di-(2,3-methylbutyl)amino]ethyl}-1-phenyl-1H-thiazino[4,3-a]indol-4-ol.

* * * * *